(12) United States Patent
Fu et al.

(10) Patent No.: US 12,109,049 B2
(45) Date of Patent: Oct. 8, 2024

(54) BLOOD PRESSURE MEASUREMENT METHOD AND APPARATUS

(71) Applicant: Kayden Beibei Fu, Rockville, MD (US)

(72) Inventors: Kayden Beibei Fu, Rockville, MD (US); Liming Fu, Guilin (CN)

(73) Assignee: Kayden FU, Rockville, MD (US)

( * ) Notice: Subject to any disclaimer, the term of this patent is extended or adjusted under 35 U.S.C. 154(b) by 864 days.

(21) Appl. No.: 17/214,849

(22) Filed: Mar. 27, 2021

(65) Prior Publication Data

US 2021/0212637 A1    Jul. 15, 2021

Related U.S. Application Data

(63) Continuation-in-part of application No. 16/032,047, filed on Jul. 10, 2018, now Pat. No. 10,966,664.

(51) Int. Cl.
| | |
|---|---|
| *A61B 5/00* | (2006.01) |
| *A61B 5/0205* | (2006.01) |
| *A61B 5/022* | (2006.01) |
| *G06F 16/23* | (2019.01) |
| *G16H 50/30* | (2018.01) |
| *A61B 5/024* | (2006.01) |

(52) U.S. Cl.
CPC .......... *A61B 5/7203* (2013.01); *A61B 5/0205* (2013.01); *A61B 5/022* (2013.01); *A61B 5/7225* (2013.01); *A61B 5/741* (2013.01); *A61B 5/743* (2013.01); *G06F 16/2379* (2019.01); *G16H 50/30* (2018.01); *A61B 5/02405* (2013.01)

(58) Field of Classification Search
CPC ..... A61B 5/7203; A61B 5/0205; A61B 5/022; A61B 5/7225; A61B 5/741; A61B 5/743; A61B 5/02405; G16H 50/30; G06F 16/2379
See application file for complete search history.

(56) References Cited

U.S. PATENT DOCUMENTS

| | | | |
|---|---|---|---|
| 2019/0000395 A1* | 1/2019 | Fu | A61B 5/02208 |
| 2019/0374169 A1* | 12/2019 | Inoue | A61B 8/468 |
| 2019/0374170 A1* | 12/2019 | Inoue | A61B 5/743 |
| 2020/0303058 A1* | 9/2020 | Deno | G06Q 40/08 |

\* cited by examiner

*Primary Examiner* — Steven O Douglas
(74) *Attorney, Agent, or Firm* — Syncoda LLC; Feng Ma

(57) ABSTRACT

A method to determine a real-time blood pressure reference value according to the blood pressure fluctuation factor can determine a blood pressure state by the ratio of the blood pressure measurement value to the blood pressure reference value, and to display the blood pressure reference value, the blood pressure measurement value and the description information of the blood pressure state by the output device. The system, applying the method, includes a mobile terminal and a medical health monitoring system. The application program of the method is downloaded and installed through network connection and APP store or I/O device, so as to describe the user's blood pressure status based on the real-time blood pressure reference value, and report the blood pressure status information and medical advice to the user via network connection.

4 Claims, 12 Drawing Sheets

BLOOD PRESSURE MEASUREMENT METHOD AND APPARATUS

CROSS-REFERENCE TO RELATED APPLICATION

This is a continuation-in-part application of U.S. patent application Ser. No. 16/032,047 filed on Jul. 10, 2018, the disclosure of which is hereby incorporated by reference in its entirety.

BACKGROUND

Blood pressure is an important parameter of human vital signs. Blood pressure detection methods can include invasive measurements and non-invasive indirect measurements. Mainstream methods of non-invasive indirect measurements include the Korotkoff sound and the oscillometric method, both producing not-time-specific random blood pressure measurements.

SUMMARY

The embodiments of the present disclosure provide a method for describing blood pressure status based on real-time blood pressure reference values. According to blood pressure fluctuation factor information such as age, gender, measurement season, and measurement time, the real-time blood pressure reference value is dynamically determined. The ambulatory blood pressure reference value is the comparison benchmark for the blood pressure measurement value, referring to the hypertension evaluation standard issued by the WHO. The ratio of the blood pressure measurement value to the blood pressure reference value is used to describe the blood pressure state of the measurer, and the blood pressure measurer is provided with reference information for judging the blood pressure state consistent with his/her vital signs and health status.

One or more embodiments of the present disclosure provide a method for determining a real-time blood pressure reference value, which includes obtaining the user's blood pressure fluctuation factor information (age, gender, measurement date, and measurement time) and searching the respective database to obtain blood pressure fluctuation value $\Delta BP$, which is needed to determine the blood pressure reference value according to the algorithm $BP_{ref}=BP_{ideal}+\Delta BP$.

One or more embodiments of the present disclosure provide a method for removing inaccurate blood pressure measurement values by obtaining the heart rate measurement value of the user, and comparing the real-time heart rate with the average heart rate to remove the inaccuracy.

One or more embodiments of the present disclosure provide a method of using an output device to indicate and describe blood pressure status to the user, including using an output device (such as a display screen) to display blood pressure measurement values and blood pressure reference values, and using text, icons, voice, and/or noise outputs to describe the user's blood pressure status.

One or more embodiments of the present disclosure also provide methods for storing algorithms, instructions, and databases (blood pressure fluctuation values, average heart rate) of blood pressure reference values, including storing the instructions, algorithms, and database in an electronic device that can be accessed by a processor. Storage media includes non-transitory storage media and non-volatile storage media.

One or more embodiments of the present disclosure also provide an algorithm for determining a blood pressure reference value: blood pressure reference value ($BP_{ref}$)= ideal blood pressure reference value ($BP_{ideal}$)+blood pressure fluctuation value ($\Delta BP$), in which $\Delta BP$ includes but is not limited to age/blood pressure fluctuation value ($\Delta BP_{age}$), the date/blood pressure fluctuation value ($\Delta BP_{date}$) and the measurement hour/blood pressure fluctuation value ($\Delta BP_{hour}$). The blood pressure reference value algorithm is expressed as $BP_{ref}=BP_{ideal}+\Delta BP_{age}+\Delta BP_{date}+\Delta BP_{hour}$.

The present disclosure also discloses a method for compensating and correcting the blood pressure reference value $\Delta BP_{ref}$ according to the ambient temperature. Relevant studies have shown that the seasonally changing ambient temperature reduces human body functions to a state of tension and has significant impacts on blood pressure fluctuations. The temperature of the environment also affects blood pressure fluctuations. Temperature (in degrees Celsius) and blood pressure fluctuations are negatively correlated. For every 1 degree Celsius drop in temperature, blood pressure rises by 0.027 mmHg. By setting up communication equipment in the electronic sphygmomanometer to obtain the ambient temperature (e.g. setting up a temperature sensor on the sphygmomanometer), establishing a mathematical model of blood pressure fluctuations and environmental temperature, one may compensate for and correct the influence of temperature changes on blood pressure fluctuations.

One or more embodiments of the present disclosure also provide a specific algorithm for judging the blood pressure state by the ratio of blood pressure measurement value/blood pressure reference value ($BP_{ratio}=BP/BP_{ref}$), including the blood pressure measurement value <blood pressure threshold value and/or blood pressure measurement value ≥blood pressure threshold value, and/or the ratio of blood pressure measurement value/real-time blood pressure reference value $BP_{ratio}=BP/BP_{ref}$. The method of describing the blood pressure state is as follows:

When $SBP_{ratio}<0.75$ and/or $DBP_{ratio}<0.75$, or SBP<90 mmHg and/or DBP<60 mmHg, the blood pressure value is determined to be low;

When $0.75 \leq SBP_{ratio}<0.875$ and/or $0.75 \leq DBP_{ratio}<0.875$, the blood pressure value is determined to be in the lower range of normalcy;

When $0.875 \leq SBP_{ratio}<1.08$ and/or $0.875 \leq DBP_{ratio}<1.08$, the blood pressure value is determined to be normal;

When $1.08<SBP_{ratio}<1.17$ and/or $1.08<DBP_{ratio}<1.125$, the blood pressure value is determined to be in the higher range of normalcy;

When $SBP_{ratio} \geq 1.17$ and/or $DBP_{ratio} \geq 1.125$, or SBP≥160 mmHg and/or DBP≥95 mmHg, the blood pressure value is determined to be high.

One or more embodiments of the present disclosure also provide a method to eliminate inaccurate blood pressure measurements. Statistical data shows that "white coat syndrome" accounts for about 20% of the population, in which heart rate and blood pressure increase in medical settings. Physical activity (exercise) also increases heart rate, causing blood pressure to increase. These are all sources of inaccuracy. The present disclosure eliminates these inaccuracies in blood pressure measurement value by using the ratio of real-time heart rate to the average heart rate ($HR_{ratio}=HR/HR_{average}$). $HR_{average}$ is the arithmetic average of the latest 10 heart rate records of the user. When $HR_{ratio} \geq 110\%$, the blood pressure measurement is deemed inaccurate; the program stops and prompts the user to re-measure blood pressure.

The present disclosure discloses another method for removing false blood pressure measurement values caused by inappropriate arm placement during measurement. It is technical common knowledge that an arm position higher or lower than the heart level during blood pressure measurement will cause inaccuracies in blood pressure measurement values. The present disclosure will adjust for these inaccuracies through methods such as setting an angle sensor on the upper arm cuff of the sphygmomanometer, which monitors the angle between the arm (axis) and the perpendicular line to the ground, allowing values to be adjusted to compensate for overestimation or underestimation when appropriate. When the sphygmomanometer is used for the first time, the user measures the angle value of the blood flow cut-off point corresponding to the height of the heart, record and store the information in the storage medium, as the angle comparison benchmark for subsequent blood pressure measurement.

The method also includes setting a distance sensor (including but not limited to ultrasonic distance sensor) on the body of the wrist sphygmomanometer. By comparing the distance from the blood flow cut-off point to an indoor reference object (such as the ceiling) with the distance from the heart to that indoor reference object, at the first time when the blood pressure meter is used, the wrist blood pressure meter is placed at the same height as the heart, and the distance between the body of the sphygmomanometer and the reference object is measured and stored as a comparison benchmark for subsequent blood pressure measurement to realize the information prompt function of the altitude of the blood flow cut-off point relative to the position of the heart.

One or more embodiments of the present disclosure provide computer-readable storage media storing algorithms, instructions, and databases, including non-transitory storage media and non-volatile storage media.

Algorithms, instructions, and databases are stored in non-transitory storage media, including blood pressure reference value algorithm, heart rate average algorithm, databases, algorithm describing blood pressure status, and program instructions. The instructions and algorithms are loaded and executed by the CPU:

The aforementioned instruction includes searching the corresponding blood pressure fluctuation value database, and determining the blood pressure fluctuation value ΔBP corresponding to the blood pressure fluctuation factor;

The aforementioned databases include, but are not limited to: age (gender)/blood pressure fluctuation value $\Delta BP_{age}$ database, measurement hour/blood pressure fluctuation value $\Delta BP_{hour}$ database, month/blood pressure fluctuation value $\Delta BP_{date}$ database, and average heart rate $HR_{average}$ database;

The aforementioned instruction includes determining the real-time blood pressure reference value according to the real-time blood pressure reference value algorithm $BP_{ref} = BP_{ideal} + \Delta BP_{age} + \Delta BP_{date} + \Delta BP_{hour}$;

The aforementioned instruction includes removing the false blood pressure measurement value according to the ratio of the real-time heart rate to the average heart rate $HR_{ratio} = HR/HR_{average}$;

The aforementioned instruction includes determining the blood pressure state according to the ratio of the blood pressure measurement value to the real-time blood pressure reference value $BP_{ratio} = BP/BP_{ref}$.

The blood pressure reference value, blood pressure measurement value, heart rate measurement value, heart rate average value, and blood pressure state description data are stored in a non-volatile access storage medium, and the data storage and reading are loaded and executed by the processor.

One or more embodiments of the present disclosure also includes the use of an application as a method for describing the blood pressure state based on the real-time blood pressure reference value, specifically in the mobile terminal. Users can download and install a mobile application from the application store and/or cloud server. When the mobile terminal (mobile terminals include, but are not limited to, smart phones, tablet computers, laptop computers, etc.) obtains relevant user data/information, it can describe the blood pressure status and give medical advice using the aforementioned methods of the present disclosure, so that people in different places (e.g. distant family members, relatives) can understand the blood pressure measurement and the blood pressure status of the user. This component of the present disclosure complements existing sphygmomanometers on the market by making up for the shortcomings of existing sphygmomanometers.

The mobile terminal receives data signals (from any electronic sphygmomanometers with network transmission function, or receives data signals sent by users through their own equipment, including data, text, and pictures input by the user) and obtains information including the age, gender, measurement date, measurement hour, blood pressure measurement value, and heart rate measurement value.

The mobile terminal CPU executes the instructions and algorithms in the mobile application, calculates and displays the real-time blood pressure reference value generated based on the acquired data, determines the blood pressure status by the aforementioned method, and displays the blood pressure reference value, blood pressure measurement value, and blood pressure status description. Outputs to enhance said description, such as voice, graphics, and/or sounds, can be relayed through an audio device.

The present disclosure also provides an online/internet-based medical health monitoring system embedded with a method for describing blood pressure status based on real-time blood pressure reference values, including a data transmission system, a network server, and terminal equipment:

The application program is downloaded and installed from computer readable storage media such as the internet, App store, cloud server, etc., including but not limited to importing and installing the application program from a mobile storage medium (U disk), I/O data interface.

The network server includes an application server and a database server. The application server receives the data transmitted by the database server. The database server stores the user's blood pressure status and associated information, including age, gender, blood pressure, heart rate, and blood pressure status records.

The user's real-time blood pressure measurement data is output through the serial port, processed into a data packet that meets the wireless communication standard, and the signal is transmitted through data communication;

Data transmission methods include but are not limited to optical fiber, Bluetooth, Wi-Fi, and GPRS;

The network server has an independent IP address and an open port, and receives any user data requesting connection;

The terminal equipment includes a computer equipment of the Internet-based medical and health monitoring system local area network.

The storage device of the medical health monitoring system is suitable for storing several instructions, including non-transitory memory and non-volatile random-access memory. The instructions loaded and executed by the CPU are included but not limited to the following:

Obtain the user's blood pressure measurement real-time data information;

According to the blood pressure fluctuation factor, search the blood pressure fluctuation value database to obtain the blood pressure fluctuation value $\Delta BP$;

Determine the real-time blood pressure reference value according to the algorithm $BP_{ref}=BP_{ideal}+\Delta BP=BP_{ideal}+\Delta BP_{age}+\Delta BP_{date}+\Delta BP_{hour}$;

Eliminate false blood pressure measurements based on the ratio of real-time heart rate to average heart rate $HR_{ratio}$;

The blood pressure status is determined according to the ratio $BP_{ratio}$ of the blood pressure measurement value to the real-time blood pressure reference value.

One or more embodiments of the present disclosure provide an electronic sphygmomanometer with a method of describing a blood pressure state. The said method is based on a real-time blood pressure reference value. The sphygmomanometer includes a CPU, a storage medium, a blood pressure (heart rate) data acquisition unit, a display, and a voice signal output device, which are characterized as follows:

The CPU is set to search the blood pressure fluctuation value database to obtain the blood pressure fluctuation values $\Delta BP_{age}$, $\Delta BP_{date}$ and $BP_{hour}$;

The real-time blood pressure reference value is given by the algorithm $BP_{ref}=BP_{ideal}+\Delta BP_{age}+\Delta BP_{hour}+\Delta BP_{date}$;

The blood pressure reference value ($BP_{ref}$) is assigned as the precondition for obtaining the blood pressure (heart rate) measurement value BP (HR);

Inaccurate blood pressure measurements determined by the heart rate fluctuation ratio $HR_{ratio} \geq 110\%$ are eliminated;

The blood pressure status description is determined by the blood pressure measurement value/real-time blood pressure reference value ratio $BP_{ratio}=BP/BP_{ref}$;

The display includes, but is not limited to, the real-time blood pressure reference value, the blood pressure measurement value, a description of the blood pressure state (including graphics and voice/sound outputs, where voice includes real and analog voice.)

The database includes but is not limited to the age (gender)/blood pressure fluctuation value $\Delta BP_{age}$ database, the measurement hour/blood pressure fluctuation value $\Delta BP_{hour}$ database, and the month/blood pressure fluctuation value $\Delta BP_{date}$ database;

The CPU is set to find the corresponding blood pressure fluctuation value $\Delta BP$ data from the "gender (age), date, measurement hour/blood pressure fluctuation value database".

"Gender, age/blood pressure fluctuation value database" is the blood pressure fluctuation value database corresponding to male and female gender and age, including but is not limited to a fluctuation value mathematical graph and data table;

"Date/blood pressure fluctuation value database" consists of the blood pressure fluctuation values of each integer month, including but is not limited to a fluctuation value mathematical graph and data table;

The "measurement hour/blood pressure fluctuation value database" consists of the blood pressure fluctuation value data set corresponding to each hour of the day, including but is not limited to a fluctuation value mathematical graph and data table.

The data storage medium of "age (gender), date, measurement hour/blood pressure fluctuation value database" includes but is not limited to non-temporary storage medium ROM.

The instruction includes judging the blood pressure state according to the ratio $BP_{ratio}$ of the blood pressure measurement value to the real-time blood pressure reference value:

Description of the blood pressure state is determined by examining the following equation: blood pressure measurement value <blood pressure threshold value and/or blood pressure measurement value & blood pressure threshold value, and/or by examining the ratio of blood pressure measurement value/real-time blood pressure reference value ($BP_{ratio}=BP/BP_{ref}$);

When $SBP_{ratio}<0.75$ and/or $DBP_{ratio}<0.75$, or in that case that SBP<90 mmHg and/or DBP<60 mmHg, the blood pressure value is determined to be low;

When $0.75 \leq SBP_{ratio}<0.875$ and/or $0.75 \leq DBP_{ratio}<0.875$, the blood pressure value is determined to be in the lower range of normalcy;

When $0.875 \leq SBP_{ratio}<1.08$ and/or $0.875 \leq DBP_{ratio}<1.08$, the blood pressure value is determined to be normal;

When $1.08 \leq SBP_{ratio}<1.17$ and/or $1.08 \leq DBP_{ratio}<1.125$, the blood pressure value is determined to be in the higher range of normalcy;

When $SBP_{ratio} \geq 1.17$ and/or $DBP_{ratio} \geq 1.125$, or SBP≥160 mmHg and/or DBP≥95 mmHg, the blood pressure value is determined to be high.

The age and gender data input methods include but are not limited to key input, touch screen input, and voice input. In addition, such data are stored in a non-volatile storage medium after the initial input by the user, such as FLASH and EEPROM, the processor executes the retrieval of age and gender data during subsequent blood pressure measurements, and the processor automatically updates the age value according to the system clock/calendar, eliminating the inconvenience of inputting age and gender information during each use.

The present disclosure contains significantly effective features that provide a method of describing blood pressure status based on real-time blood pressure reference value. The method overcomes the technical defects of existing electronic sphygmomanometers and can provide a more accurate and personalized user experience. The blood pressure state description provides useful medical and healthcare reference information while the unique display interface shows users the real-time blood pressure reference value, which encourages people to pay attention to the influence of blood pressure fluctuation factors, demystifying the common misconceptions around an inaccurate measurement. Moreover, the CPU executes unique program operating instructions to obtain the user's age and gender data (to assign a real-time blood pressure reference value) as a precondition to start blood pressure measurement, and eliminates blood pressure inaccuracies with reference to the heart rate ratio, improving the accuracy of the measurement and the blood pressure state description. To a certain extent, the simple, artificially intelligent sphygmomanometer can simulate the consultation process of a health professional, providing upgraded medical services of a specialist level for users.

DETAILED DESCRIPTION

Figure 1:
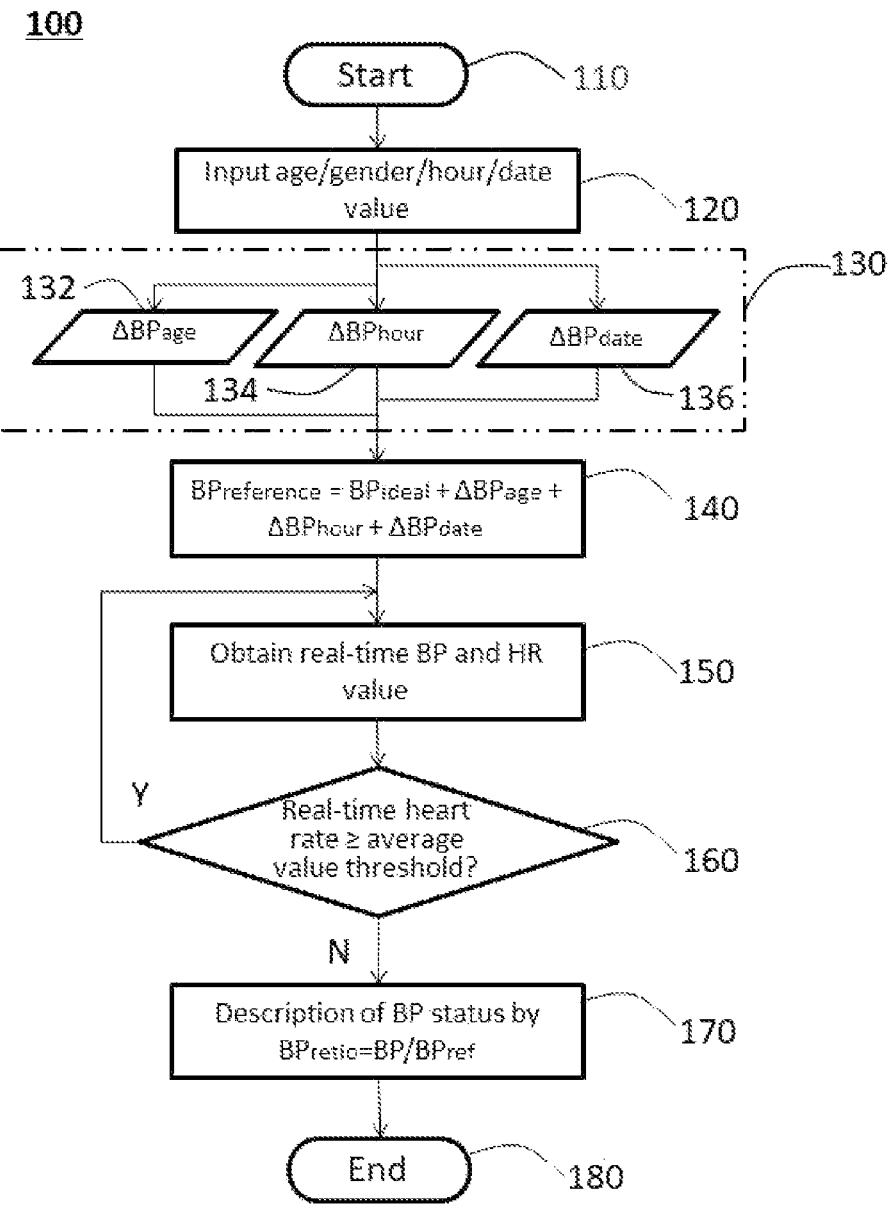
FIG. 1 is a program flow chart showing the method of describing blood pressure status based on real-time blood pressure reference value.

The specific implementation of the present disclosure will be described in detail below with reference to the drawings.

With the emergence of new technologies (such as cuffless blood pressure measurement through light wave detection), blood pressure all-weather monitoring (ABPM) and health monitoring networks have become the new method for blood pressure measurement. Although ABPM is an improved method for monitoring and evaluating blood pressure status, it comes with inevitable interferences to daily life. Therefore, ABPM is mainly used for patients who have been diagnosed with high blood pressure, and it is difficult for ABPM to become the mainstream method of blood pressure monitoring. As such, the general population still uses random blood pressure measurement methods.

The World Health Organization (WHO) and the European Union have issued a high blood pressure identification value of ≥140/90 mmHg, and the United States has revised it to 130/80 mmHg. Although WHO and other authorities have not released data for the standard blood pressure, the health care industry generally agrees with a standard blood pressure reference value ($BP_{ideal}$) of 120/80 mmHg, and with the following:

A systolic blood pressure <90 mmHg or diastolic blood pressure <60 mmHg indicates hypotension;

A 90 mmHg≤systolic blood pressure<105 mmHg or 60 mmHg≤diastolic blood pressure<70 mmHg indicates a low to normal blood pressure value;

A 105 mmHg≤systolic blood pressure<130 mmHg or 70 mmHg≤diastolic blood pressure<85 mmHg indicates a normal blood pressure value;

A 130 mmHg≤systolic blood pressure<140 mmHg or 85 mmHg≤diastolic blood pressure<90 mmHg indicates a normal to high blood pressure value;

A systolic blood pressure≥140 mmHg and diastolic blood pressure≥90 mmHg indicate hypertension.

Based on the above-mentioned blood pressure standard values and the general consensus for determining blood pressure states, the existing electronic sphygmomanometers use 120/80 mmHg as the blood pressure reference value to determine and describe the user's blood pressure state.

Among the household users who use electronic sphygmomanometers to monitor blood pressure, a large proportion of people think that electronic sphygmomanometers are "inaccurate". The inaccuracy not only confuses users, but also directly affects the efficiency and reliability of electronic sphygmomanometers as a family healthcare tool. However, when used in medical institutions and settings, there are almost no doubts regarding the accuracy of electronic sphygmomanometers. Several factors contribute to the above confusions.

There is a correlation between blood pressure and age. According to a research paper published by Lancet, the global average blood pressure for men was 127/79 mm Hg and 122/77 mm Hg for women in 2015.

Researchers from the National Center for Health Statistics studied the average blood pressure of American adults from 2001 to 2008, and they had the following findings breakdown by age and gender:

Average male blood pressure: 18-39 years old: 119/70 mmHg; 40-59 years old: 124/77 mmHg; 60 years old and above: 133/69 mmHg.

Average female blood pressure: 18-39 years old: 110/68 mmHg; 40-59 years old: 122/74 mmHg; 60 years old and above: 139/68 mmHg.

Figure 7:
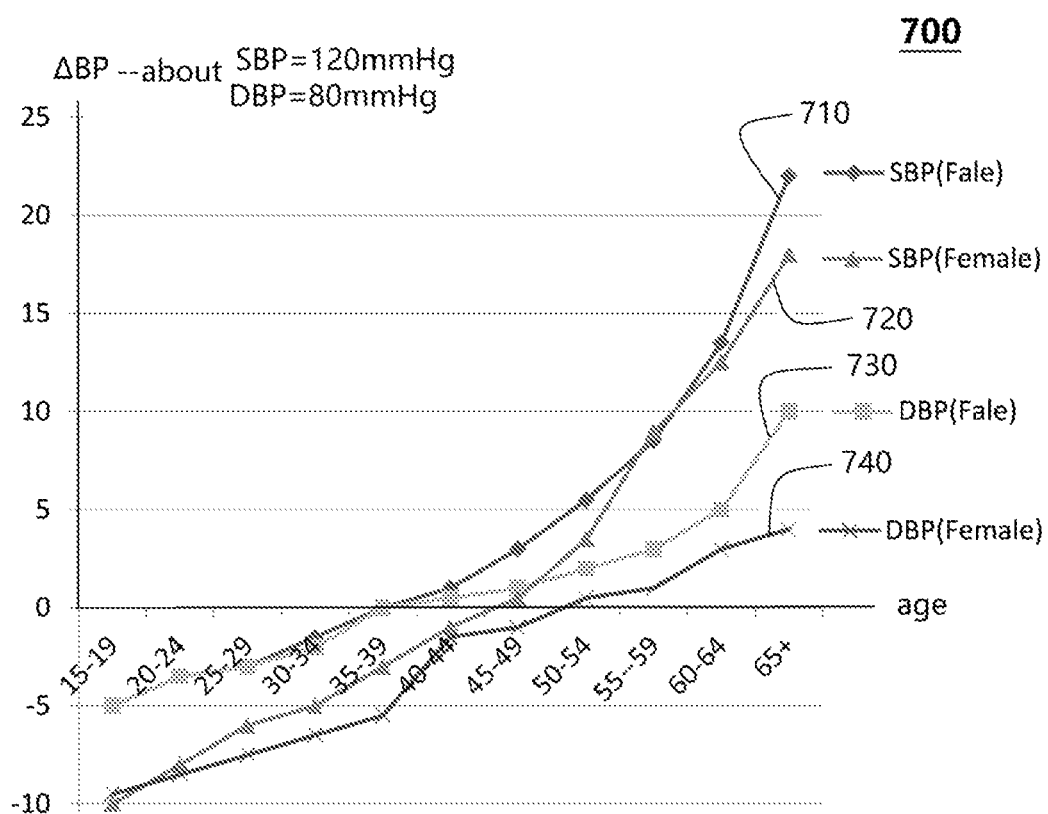
FIG. 7 is a graph of age (gender)/blood pressure fluctuation value.

Although WHO and other authoritative organizations have not released age-related blood pressure reference values, the fluctuation of blood pressure with age has been confirmed by a large number of research results and public literature. The correlation between blood pressure fluctuations and age is shown in FIG. 7, in which the male systolic blood pressure/age and a fluctuation curve is shown by reference numeral 710, the diastolic blood pressure/age fluctuation curve is shown by numeral 730, the female systolic blood pressure/age fluctuation curve is shown by numeral 720, and the diastolic blood pressure fluctuation curve is shown by numeral 740.

The influence of seasons on blood pressure fluctuations is also very obvious. A public literature piece published by the Omron Corporation of Japan shows that the influence of temperature change on blood pressure fluctuations is 0.027 mmHg/° C., and the correlation between blood pressure and temperature is inversely proportional (blood pressure fluctuations in winter and summer are about 7 mmHg), and is not affected by age, gender and geographic location.

Figure 8:
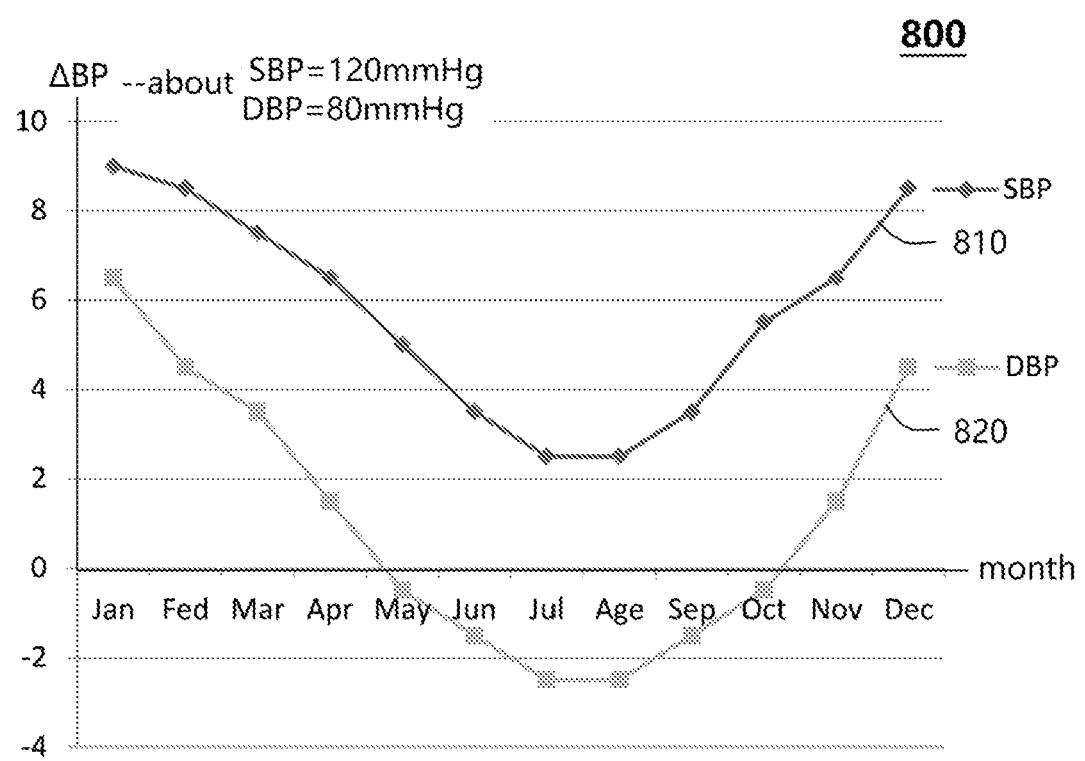
FIG. 8 is a graph of date (month)/blood pressure fluctuation value.

The publication titled "Weather-Related Changes in 24-Hour Blood Pressure Profile Effects of Age and Implications for Hypertension Management" by Pietro Amedeo Modesti, et. al disclosed that fluctuations in blood pressure reach a peak in winter (December, January), while in the summer (July, August), the blood pressure fluctuations drop to its minimum. The systolic blood pressure fluctuation curve is shown in FIG. 8 with reference number 810, and the diastolic blood pressure fluctuation curve is shown with reference number 820.

Figure 9:
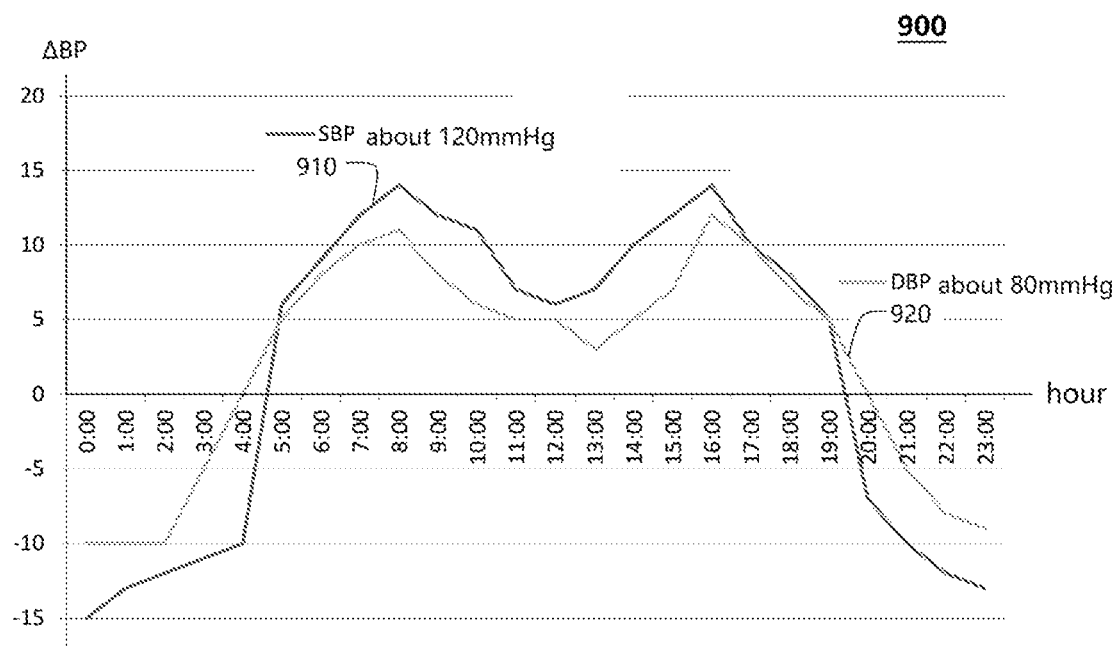
FIG. 9 is a graph of measurement hour/blood pressure fluctuation value.

Blood pressure fluctuations in one day (24 hours) is similarly obvious. Kazuomi Kario etc., disclosed in a paper titled "Changes in 24-Hour Patterns of Blood Pressure in Hypertension Following Renal Denervation Therapy" that the blood pressure fluctuates to the highest value from 6:00 to 10:00 and from 15:00 to 17:00, and the lowest blood pressure appears from 10:00 to 2:00 in the evening. The systolic blood pressure fluctuation curve is shown in FIG. 9 with reference number 910, and the diastolic blood pressure fluctuation curve is shown in reference number 920.

The above-mentioned sources confirm that blood pressure fluctuation factors include age, gender, season, and time. There are significant differences in the random blood pressure measurement values of ordinary people (those with healthy blood pressure), and the blood pressure fluctuation value is up to about 30 mmHg. However, home users may not have medical knowledge and judgment. For example, a 60-year-old man measures 142/90 mmHg at 8:00 in the morning and 115/70 mmHg at 10:00 in the evening. He may feel panicked upon seeing the "high" blood pressure as indicated by existing sphygmomanometers, and may question the 115/70 mmHg blood pressure measurement. Users may subconsciously regard 120 mmHg as the normal blood pressure reference value ($BP_{ideal}$), and to make matters worse, this is confirmed by the blood pressure monitor as its reference value is also set and stagnant at 120/80 mmHg. The electronic sphygmomanometer ignores the influence of blood pressure fluctuation factors and gives users erroneous blood pressure status information, which causes doubt and panic, and contributes to the common concern that electronic sphygmomanometers are not accurate.

When measuring blood pressure for patients in medical institutions, doctors will comprehensively judge the influence of blood pressure fluctuation factors (age, gender, season, time) on blood pressure measurement values based on their medical knowledge to correctly assess the patient's blood pressure status. Therefore, there is almost no question of "uncertainty" when sphygmomanometers are used in medical institutions.

The above shows that the "inaccurate measurement" phenomenon of home-use electronic blood pressure monitors is due to inaccuracies within the physical measurement, and due to the 120/80 mmHg static blood pressure reference value in both the minds of users and as a reference value for existing electronic sphygmomanometers. It is common medical practice to correct and compensate the blood pressure reference value according to the blood pressure fluctuation factors, so these fixed blood pressure reference values cause incorrect blood pressure status judgment and incites doubt and concern, therefore raising questions about the inaccuracy of the existing electronic sphygmomanometers. Therefore, the illusion of inaccuracy is produced by defects in the technical scheme of existing electronic sphygmomanometers.

As shown in FIG. 1, a method 100 of describing blood pressure status based on real-time blood pressure reference values of the present disclosure includes determining the blood pressure fluctuation value according to the blood pressure fluctuation factor, and describing the blood pressure state according to the ratio of the blood pressure measurement value to the blood pressure reference value, which is implemented by the computing device. In step 120, the age, gender, date (month) and blood pressure measurement hour (hour) values are inputted. The date and hour data are imported from the clock unit by the processor of the computing device. The age and gender information requires manual (keyboard, touch and voice) input, and/or the importation of recorded data from the system memory. In step 130, the CPU obtains $\Delta BP$ by searching the corresponding blood pressure fluctuation value database, including $\Delta BP_{age}$ (step 132), $\Delta BP_{hour}$ (step 134), and $BP_{date}$ (step 136).

In step 140, the CPU executes the algorithm instruction $BP_{ref}=BP_{ideal}+\Delta BP_{age}+\Delta BP_{date}+\Delta BP_{hour}$ to determine the real-time blood pressure reference value.

In step 150, the user inputs instructions (including keyboard, touch screen, and voice) to start blood pressure measurement and obtain blood pressure and heart rate measurement values; in step 160, the CPU executes instructions to read the average heart rate from the storage medium and compare it with the real-time heart rate. When the ratio of real-time heart rate/average heart rate exceeds the set threshold, it is determined that the blood pressure measurement value is inaccurate, and the display prompts users to reinitiate measurement, returning to step 150 in the diagram.

In step 170, the CPU determines the blood pressure state according to the ratio $BP_{ratio}$ of the blood pressure measurement value to the real-time blood pressure reference value, and uses the blood pressure state threshold interval where the value of $BP_{ratio}$ is located to give the blood pressure state prompt information, such as "BP low", "BP normal −", "BP normal '"', "BP normal+" and "BP high".

Figure 2A:
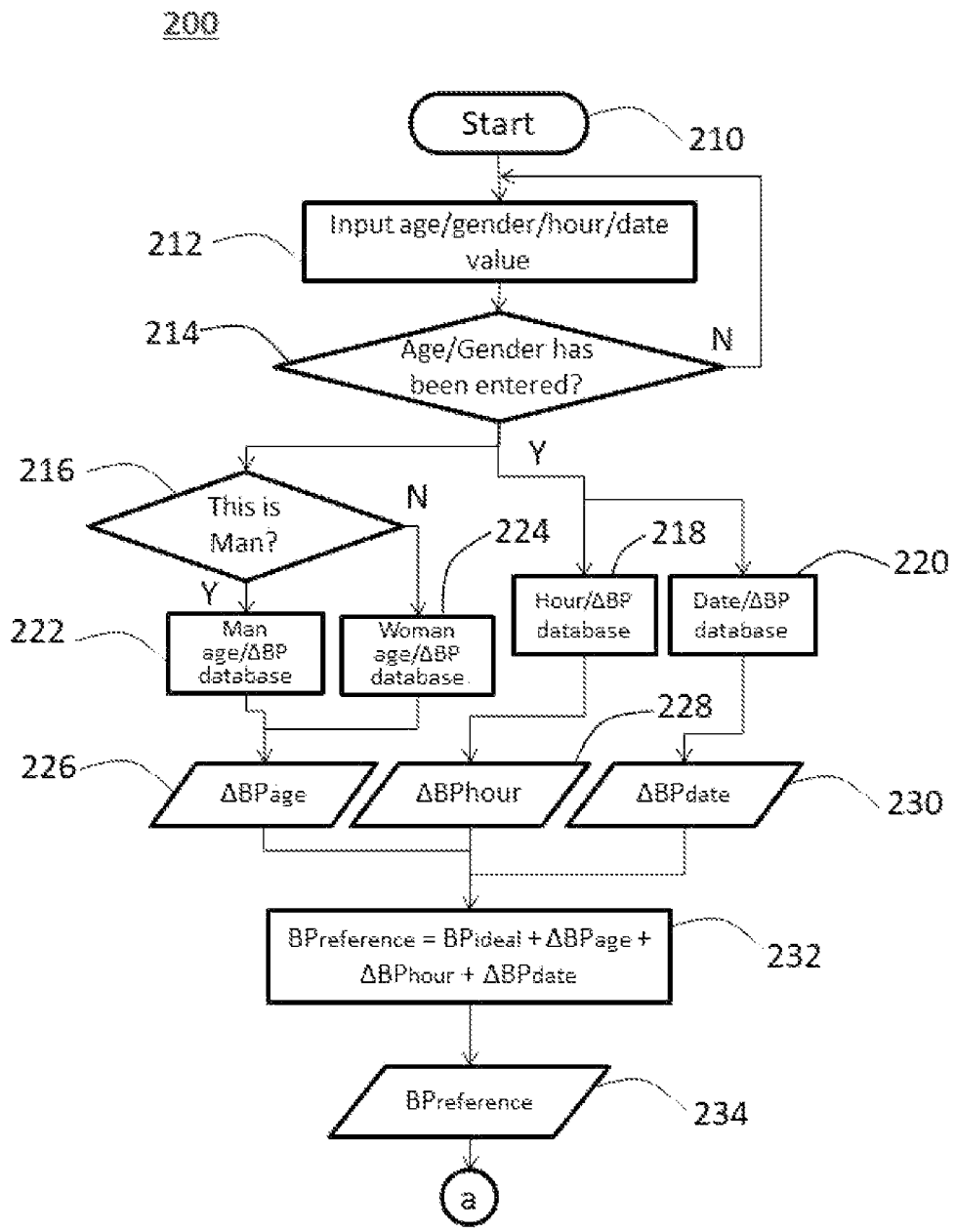
FIG. 2A is a first portion of a flowchart of an electronic blood pressure monitor application program based on the method of formulating a blood pressure status description according to real-time blood pressure reference value.
Figure 2B:
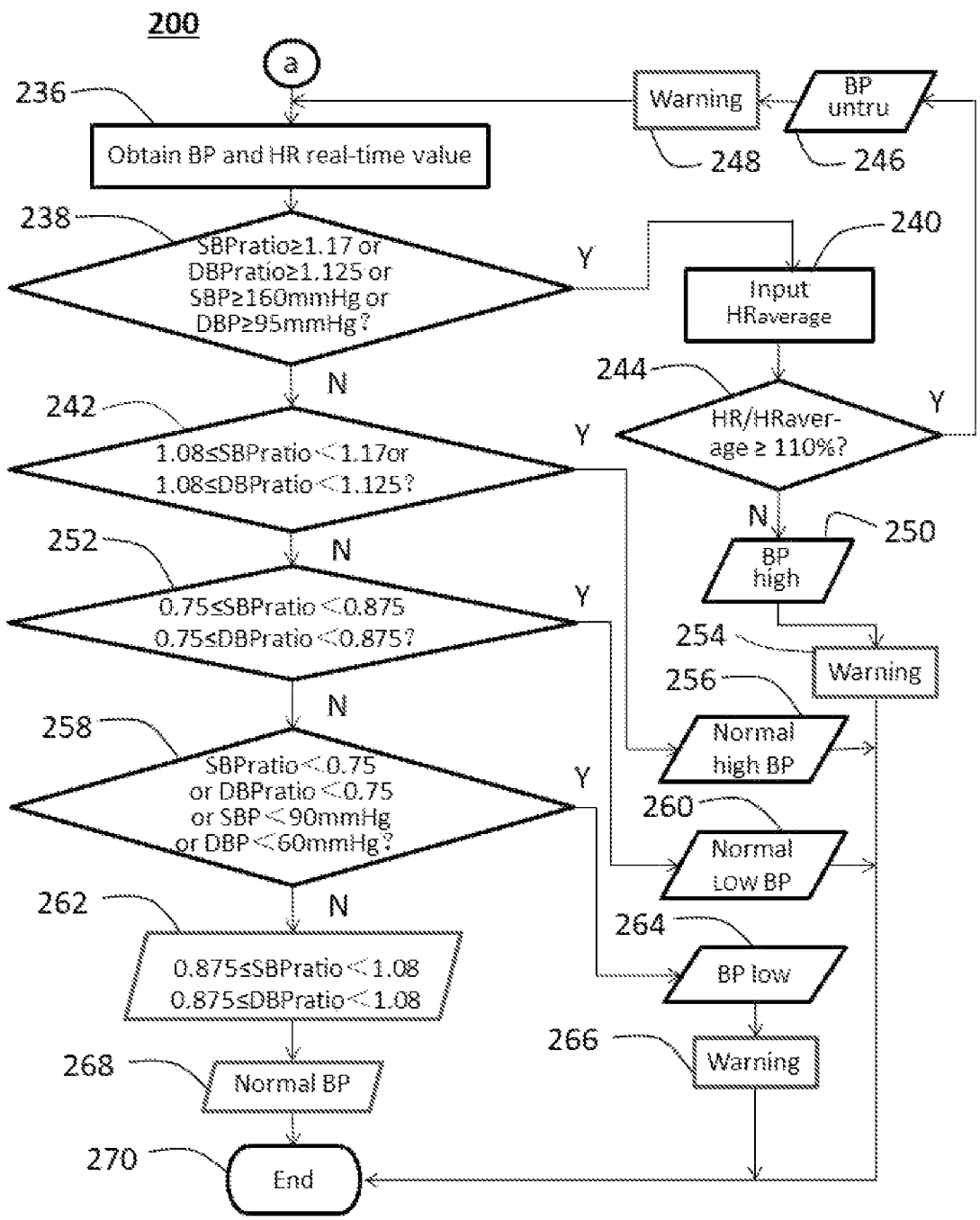
FIG. 2B is a second portion of a flowchart of an electronic blood pressure monitor application program based on the method of formulating a blood pressure status description according to real-time blood pressure reference value.
Figure 3:
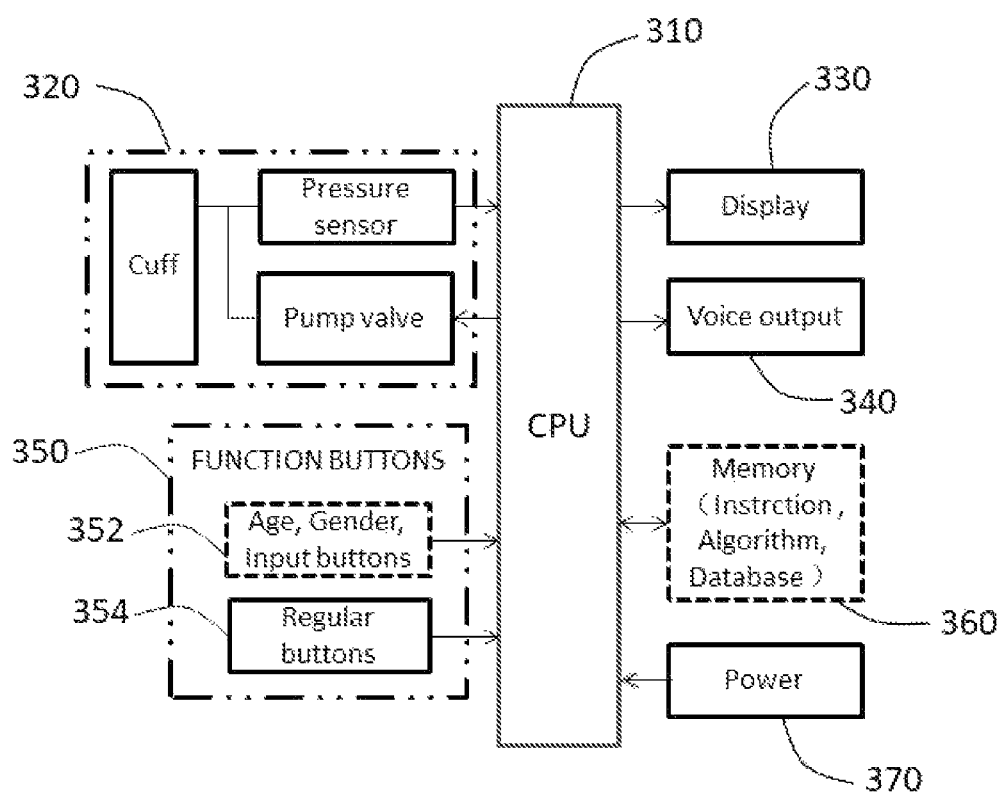
FIG. 3 is a functional block diagram of an electronic sphygmomanometer based on the method of formulating a blood pressure status description according to real-time blood pressure reference value.

The first manifestation of the method described in the present disclosure is shown in FIG. 3 (300), an electronic sphygmomanometer that utilizes real-time blood pressure reference value to describe the blood pressure state. The numbers 310, 320, 330, 340, 354 and 370 are the features and equipment common to the embodiment of the present disclosure and the existing electronic sphygmomanometers on the market. The numbers 352 and 360 are new features of the present disclosure, in which the component labeled 352 refers to the age and gender data input button (including voice input), label 360 is a computer-readable storage medium, including temporary storage medium (RAM), non-transitory storage medium (ROM) and non-volatile storage medium (EEPROM, FLASH). The storage medium 200 stores computer instructions, algorithms, and databases shown in FIG. 2A and FIG. 2B. The electronic sphygmomanometer embodying the present disclosure is different from existing electronic sphygmomanometers in its technical features, that is, while the former still uses the conventional technical methods and devices to obtain blood pressure and heart rate measurement values, the present disclosure takes into account the different factors causing blood pressure fluctuations, and includes a blood pressure reference value along with the description of the blood pressure state. Therefore, the electronic sphygmomanometer embodying the present disclosure can provide more accurate medical advice that better aligns with the real blood pressure state of the user, to an extent comparable to that from a healthcare professional.

FIG. 2A and FIG. 2B illustrate an implementation process of a technical solution provided according to some embodiments of the present disclosure. In step 210, after the system is powered on, the CPU imports the date and hour data, and the sphygmomanometer display interface displays clock data (labeled area 410 in FIG. 4). At the same time, the male icon 442 in the area labeled 440 and the default age value in the icon labeled 444 (for example, age=35, display number 35) flashes, and the system sends out a language prompt such as "Please select age and gender". Step 214 determines whether the age and gender values are input completely. If "Yes", execute step 216 to determine the gender selection, if "Yes", execute step 222, if "No", execute step 224.

Step 222 or 224 searches the age/blood pressure fluctuation value database of the corresponding gender, Step 226 obtains the age/blood pressure fluctuation value $\Delta BP_{age}$, Step 218 searches the hour/blood pressure fluctuation value database, Step 228 obtains the date/blood pressure fluctuation value $\Delta BP_{hour}$, and Step 220 searches the date/Blood pressure fluctuation value database, step 230 obtains the date/blood pressure fluctuation value $\Delta BP_{date}$. In step 232, the CPU executes the algorithm instruction, and step 234 generates a real-time blood pressure reference value $BP_{ref}$, and the blood pressure reference value is assigned and stored in the memory RAM.

After the CPU executes step 234 to obtain the real-time blood pressure reference value, the system gives a message prompt (including text display and/or voice) of "Press Start to measure blood pressure." Step 236 obtains blood pressure and heart rate measurement values, and step 238 determines whether $SBP_{ratio} \geq 1.17$ and/or $DBP_{ratio} \geq 1.125$, or that SBP≥160 mmHg and/or DBP≥95 mmHg. When one or more of the above items are "Yes", go to step 240, where the CPU reads the average heart rate ($HR_{average}$) in the non-volatile storage medium. The average heart rate is generated by averaging the latest ten data points of the user's heart rate, using the algorithm $HR_{average} = (HR_1 + HR_2 + \ldots + HR_n)/n$, where n is an integer, when $n + n_{+9} > 10$, the heart rate data storage is updated cyclically (not shown in the program flowchart 200), and the heart rate and average heart rate data are stored in a non-volatile storage medium (such as FLASH or EEPROM) and the processor executes relevant instructions.

Step 244 determines whether $HR_{ratio} = IR/HR_{average}$ is ≥110%. When one or more items are "Yes," step 246 generates a prompt such as "Heart rate exceeds normal value, blood pressure measurement value is inaccurate." In step 248, the display flashes blood pressure measurement value and issues a prompt such as "Please re-measure blood pressure," and the system returns to step 236 to re-measure blood pressure/heart rate. If step 244 arrives at "No", execute step 250 to generate a prompt such as "high blood pressure." Step 254 then executes the flashing display of the blood pressure measurement value, and displays message such as "high blood pressure, please seek medical attention" (utilizing text, icon, and/or voice output). Step 270 is then executed to end the program.

In step 238, when the result is "No", step 242 is executed to determine whether $1.08 \leq SBP_{ratio} < 1.17$ and/or $1.08 \leq DBP_{ratio} < 1.125$ is satisfied. When one or more items are "Yes", step 256 generates "normal to high blood pressure" data and the system will send out a "Normal to High Blood Pressure" message, then execute step 270 to end the program. If step 238 results in "No", execute step 252.

Step 252 determines whether $0.75 \leq SBP_{ratio} < 0.875$ and/or $0.75 \leq DBP_{ratio} < 0.875$ is satisfied. If one or more items are "Yes", step 260 generates "Normal to low blood pressure" data and the system sends out "Normal to low blood pressure" message, then execute step 270 to end the program. If step 252 results in "No", execute step 258.

Step 258 determines whether $SBP_{ratio} < 0.75$ and/or $DBP_{ratio} < 0.75$, or SBP<90 mmHg and/or DBP<60 mmHg, if one or more items are "Yes", step 264 generates "low blood pressure" data, and step 266 is executed. The blood pressure measurement value is displayed in a flashing manner and a message of "low blood pressure" is issued, then the execution of step 270 ends the program. If step 258 results in "No", step 262 is executed.

Step 262 determines values of $0.875 \leq SBP_{ratio} < 1.08$ and $0.875 \leq DBP_{ratio} < 1.08$. Step 268 is executed, the system sends out a "normal blood pressure" message prompt, and step 270 is executed to end the program.

Figure 4:
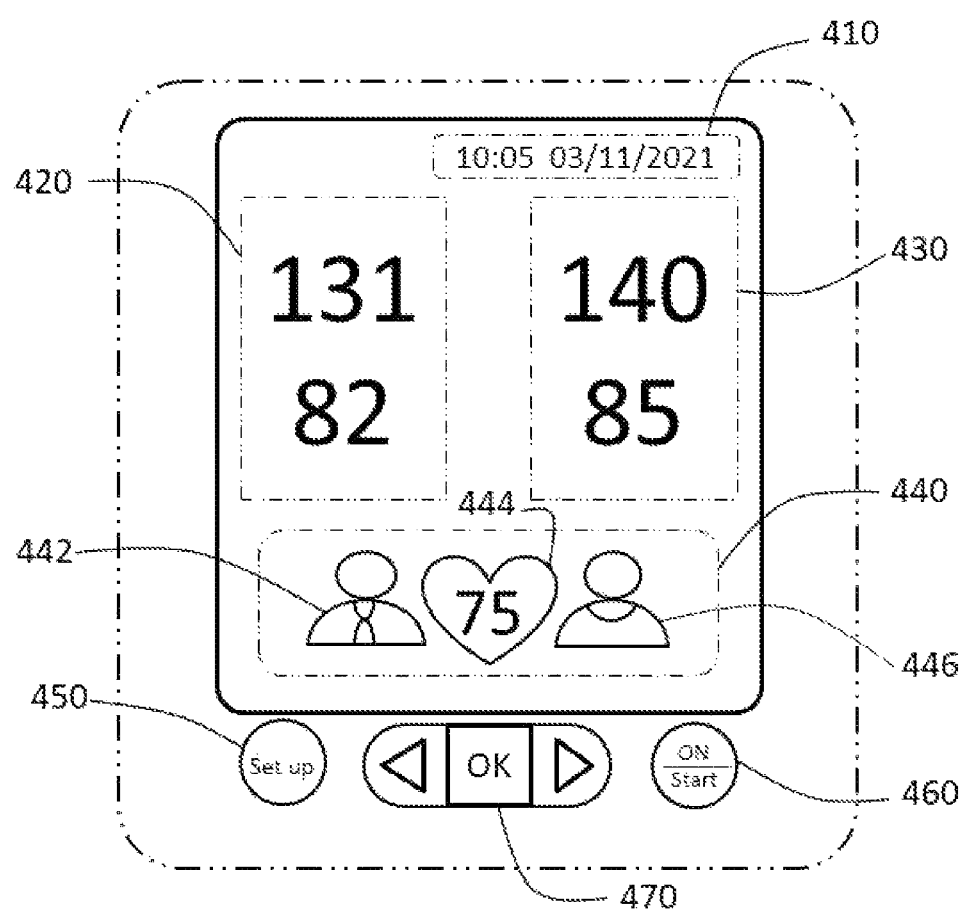
FIG. 4 is a schematic diagram of the electronic blood pressure monitor display interface.
Figure 5:
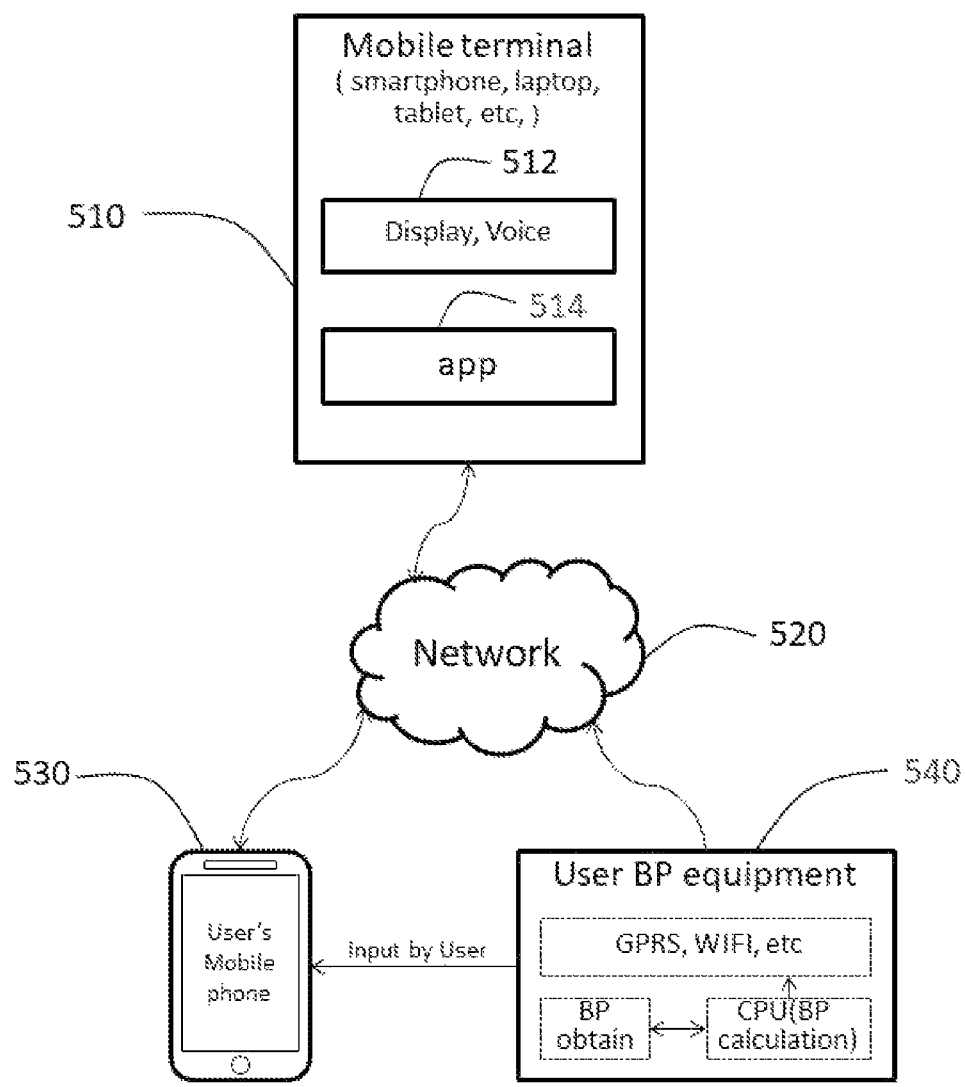
FIG. 5 is a functional block diagram of a mobile terminal based on the real-time blood pressure reference value to describe the blood pressure state method.
Figure 6:
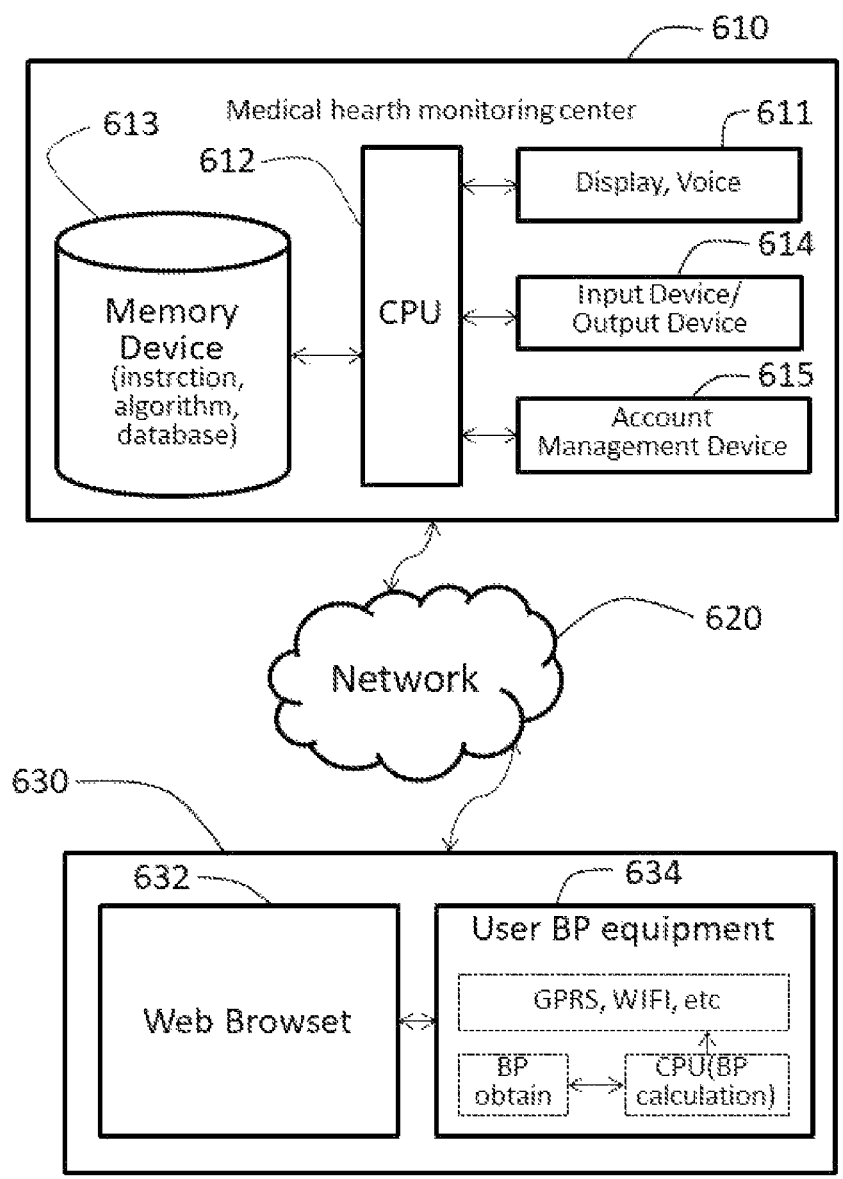
FIG. 6 is a functional block diagram of the health monitoring network based on the real-time blood pressure reference value describing the blood pressure status method.

FIG. 4 (FIG. 4) shows the display interface (400) of the embodiment of the present disclosure. The calendar and time of day are displayed in the double-dotted-line frame numbered 410, and the real-time blood pressure reference value SBP/DBP is displayed in the double-dotted-line frame numbered 420. The blood pressure measurement value SBP/DBP is displayed in the double-dotted-line frame labeled 430, and the double-dotted-line frame labeled 440 is the combined element display area. Label 442 refers to the male icon, 446 indicates the female icon, and the heart-shaped icon labeled 444 displays the age value and heart rate value sequentially. The sequence of instructions executed by the CPU is displayed.

In step 210, press the power (ON) button (labeled 460) of the electronic sphygmomanometer monitor. This executes step 212, where the display interface area (410) displays the calendar and hour, the icon labeled 442 flashes (the system default gender is male), and the number in the 444 box flashes the system default age of 35 years old. The system issues a voice or graphic message prompt of "Please select age and gender, and press the OK button to confirm." After the user selects the gender and age, the real-time blood pressure reference value is displayed in the box labeled 420, and the gender and age numbers in the box labeled 444 stop flashing.

After the user enters the age and gender information for the first time, the processor stores the information and data under the user's name (the system automatically numbers users chronologically, for up to 5 users), and the data information is stored in non-volatile access storage medium, such as FLASH and EEPROM. When the blood pressure is measured again, the processor retrieves the user's age and gender data of user number 1, and the gender and age values in the corresponding area of the display interface are displayed flashing. To reduce the inconvenience of reselecting age value at each use, the user age data is automatically updated by the processor according to the system clock/calendar.

While the blood pressure reference value (generated by step 234) is displayed in the 420 frame, the system will send out a message (voice and/or text) prompting "Press the Start key to measure blood pressure", and perform step 236 to obtain the blood pressure and heart rate measurement values. The 430 frame displays the blood pressure measurement value (SBP/DBP), while the heart rate measurement value is displayed in the 444 box. If the blood pressure measurement is judged to be abnormal such as "high blood pressure" or "low blood pressure", the SBP/DBP number in the 430 box will flash; if the heart rate measurement is judged to be an abnormal heart rate (too fast or too slow), the heart-shaped figure and the heart rate value in box 444 will flash simultaneously.

This embodiment has the function of recording blood pressure reference value, blood pressure measurement value, and blood pressure status data. Each blood pressure measurement value, blood pressure reference value, heart rate value, and blood pressure status datum is stored in non-volatile access memory (including but not limited to FLASH, EEPROM), within the set data storage limit (such as storing 10 or 100 sets of data) that is cyclically updated. When pressed, the "set up" button brings up the user history of blood pressure measurement results and blood pressure statuses. Display interface areas 410, 420, 430 and 440 display the corresponding data, including the flashing of abnormal blood pressure status.

In the second embodiment, the method of describing the blood pressure status based on the real-time blood pressure reference value is applied to the mobile terminal system (500), and the mobile terminal 510 includes but is not limited to iPhone, tablet, and laptop. Since the basic function of existing electronic sphygmomanometers is to measure blood pressure and heart rate, the basic electronic sphygmomanometer lacks even calendar and clock functions. As an improvement, the multifunctional electronic sphygmomanometers on the market have data transmission (including wired and wireless transmission methods) and data memory functions, but they only display blood pressure measurement values, heart rate measurement values, and measurement hour records in the transmitted data packets. All existing sphygmomanometers lack age and gender information, and therefore lacks any ability to correct and compensate for the blood pressure fluctuations caused by age, gender, date, and measurement hour, never mind the functions of displaying blood pressure reference values and describing blood pressure statuses.

Figure 10A:
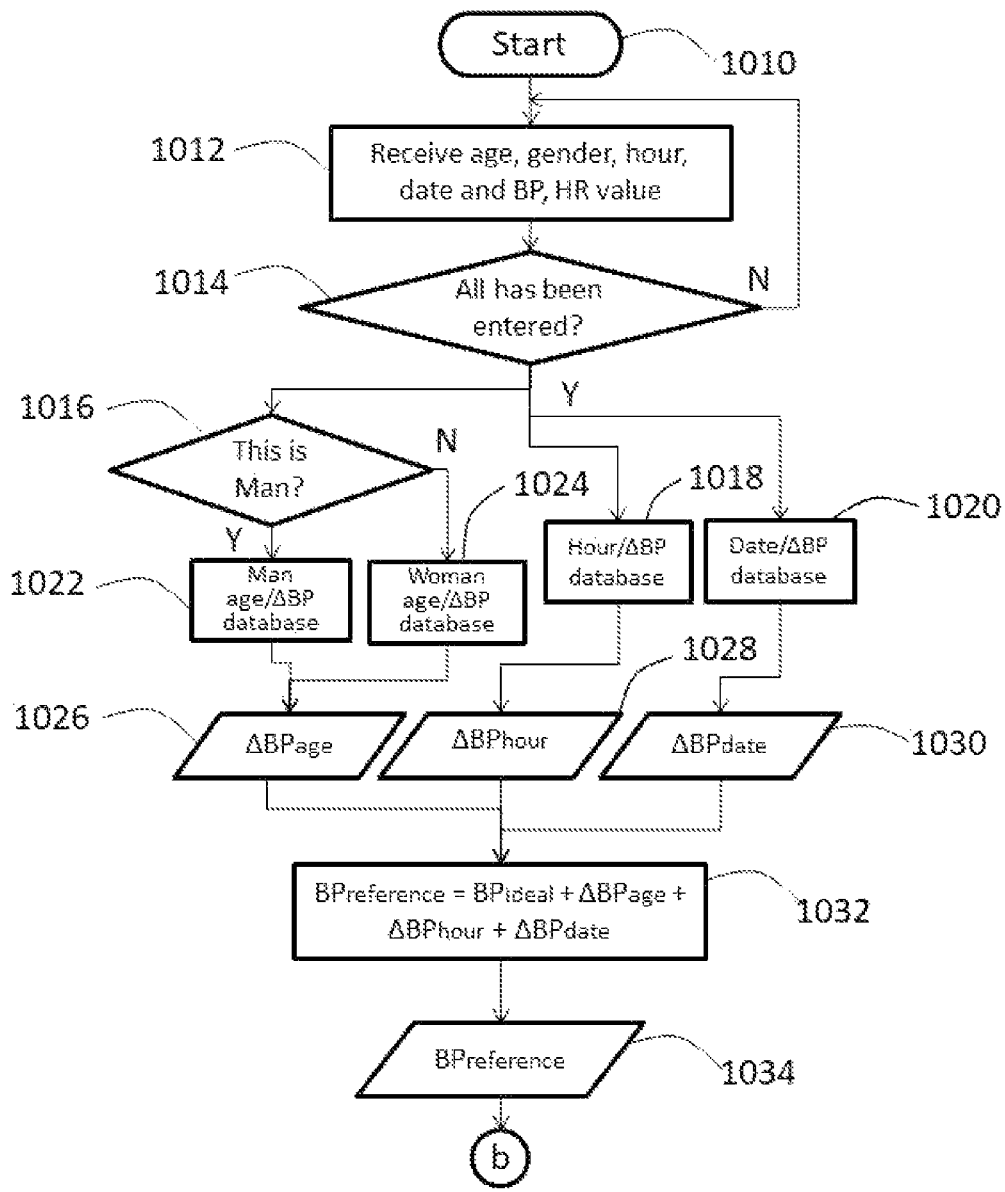
FIG. 10A is a first portion of a flow chart of the mobile terminal and medical health monitoring system application program that describes the blood pressure status method based on the real-time blood pressure reference value.
Figure 10B:
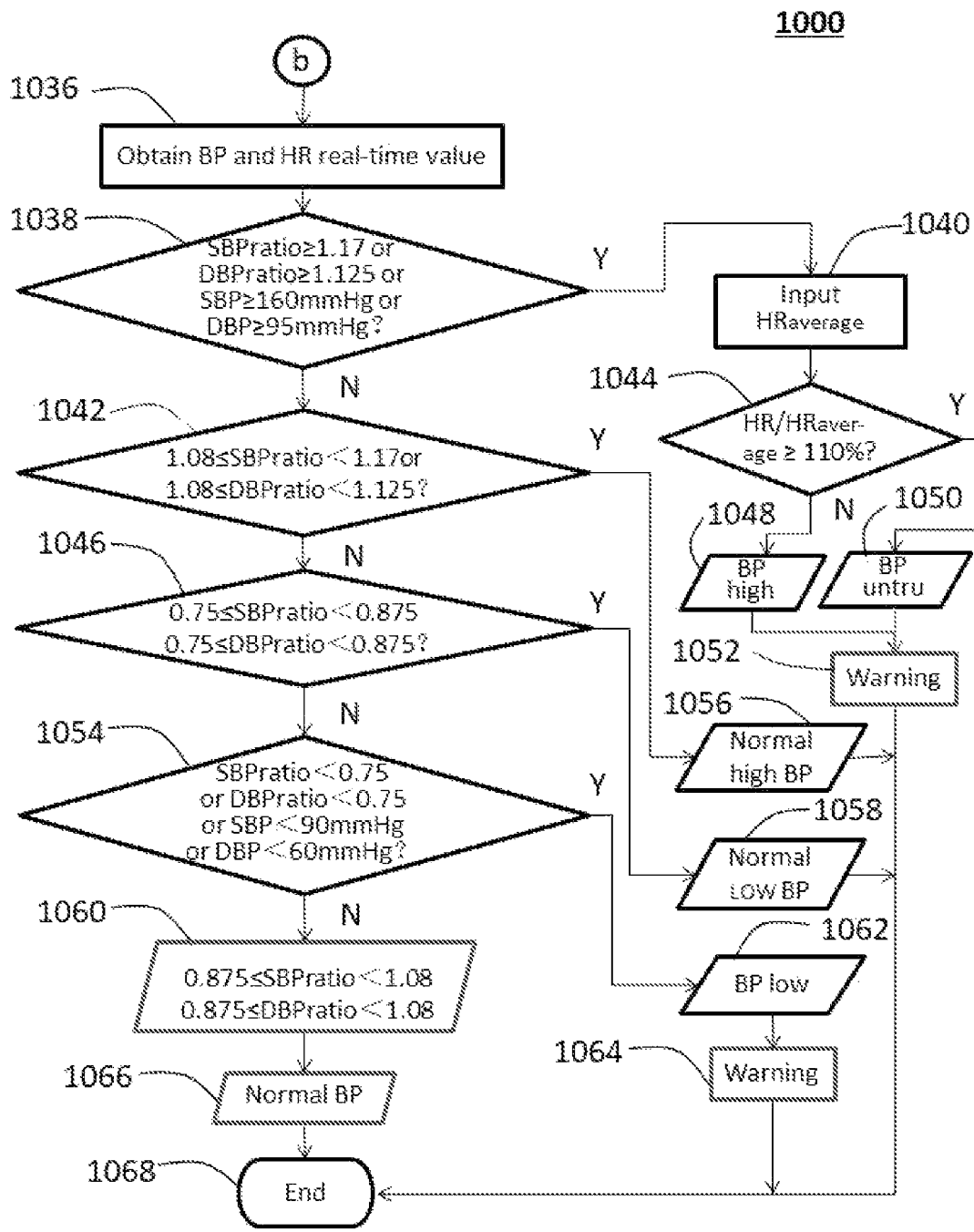
FIG. 10B is a second portion of a flow chart of the mobile terminal and medical health monitoring system application program that describes the blood pressure status method based on the real-time blood pressure reference value.

In this second embodiment, the method of describing the blood pressure state based on the real-time blood pressure reference value is made into an application program (APP) 514 suitable for downloading, installing, and running in a mobile terminal. The APP program flowchart 1000 is displayed in FIG. 10A and FIG. 10B. As shown, step 1012 receives the measured blood pressure value, heart rate value, and measurement hour data packet from the user through the application service module of the mobile terminal including the age and gender information of the blood pressure measurer entered by the user, or the mobile terminal user's supplementary entry of the age and gender information of the blood pressure measurer, or the inputs from the mobile terminal operator of the age and gender information of the requesting user, or the retrieved user age and gender information stored in the mobile terminal. In step 1014, it is determined whether the data obtained is complete. If "Yes", execute the next step and sequentially run to step 1034 to obtain the real-time blood pressure reference value $BP_{ref}$.

In steps 1036 to 1068, the blood pressure status is determined by the ratio of the blood pressure measurement value to the real-time blood pressure reference value ($BP_{ratio}$). The display device (512) of the mobile terminal displays the real-time blood pressure reference value, blood pressure measurement value, heart rate measurement value, measurement date, measurement hour, age and gender, and other related information. It may also output voice and noise signals in addition to storing the above-mentioned data information in the non-volatile storage medium (including but not limited to FLASH, EPPROM) of the mobile terminal.

In step 1052 and step 1064, the CPU executes the abnormal data warning prompt, and flashes prompts for abnormal values such as abnormal blood pressure measurement values and inaccurate blood pressure measurement values from steps 1048, 1062, and 1050.

The third embodiment of the present disclosure applies the method of describing blood pressure status based on real-time blood pressure reference value to the medical health monitoring system (600). The medical health monitoring system central server includes an application server and a database server. The application server has an independent IP address and an open port that receives connection requests and transmits data to the requesting user. The database server stores the user's identity and data information, including the recorded data on age, gender, blood pressure, and heart rate.

The real-time blood pressure measurement data of the requesting user is outputted through the serial port and the signals are transmitted through the data communication module. The data transmission methods include but are not limited to optical fiber, Bluetooth, Wi-Fi and GPRS. The terminal equipment includes the computer equipment of the network-based medical health monitoring system.

The medical health monitoring system records and stores data on the user's identity and vital signs, tracks and monitors the user's vital signs, and provides medical advice. In the medical health monitoring system, the user's blood pressure data records include ABPM data and random blood pressure measurement data, with the majority being random blood pressure measurement data because ABPM focuses on patients diagnosed with hypertension, which cannot be easily applied to the general population.

The medical health monitoring system maintains a conventional random blood pressure baseline value ($BP_{ideal}$) of 120/80 mmHg, due to the ignorance of blood pressure fluctuation factors. Therefore, there are many errors in the assessment of blood pressure status, and the provided medical advice is not valuable or can even be harmful without the verification and correction by a healthcare professional. This greatly increases the operating cost of the system and the workload of doctors. For a medical health monitoring system with a huge number of users, this seems to be a difficult workload.

In this third embodiment, an application program (1000) for describing blood pressure status based on real-time blood pressure reference values is embedded in the medical health monitoring system (600). The reference number 610 is the block diagram of the medical health monitoring center, the reference number 612 is the CPU, the reference number 611 is the display and voice output device, 613 is a storage medium, 614 is an I/O interface device, and 615 is a user account management device. Label 620 refers to a communication network, and 630 refers to a user-owned device, including blood pressure and heart rate measurement equipment, as well as signal transmission and web browsing equipment.

In the user equipment numbered 630, the user obtains the blood pressure and heart rate measurement values through the blood pressure measurement device, and transmits the data to the medical health monitoring center through the network 620 via the signal transmission device, including the blood pressure, heart rate measurement value, date, and measurement hour date. After receiving the user data, the CPU executes the instruction to execute step 1012, and stores the user data in the nonvolatile storage medium of the storage device 613 through the user account management device 615. CPU 612 also executes application program instructions and algorithms to generate user blood pressure reference value and real-time blood pressure status information and store it in the non-volatile storage medium of storage device 613, including real-time blood pressure reference value, blood pressure measurement value, heart rate measurement value, average heart rate value, the determined blood pressure status information, etc.

When the user connects to the system through the relevant equipment of the user terminal (electronic blood pressure meter with network transmission function, PC, etc.), the account management system of the system user server automatically matches the user information, and the CPU labeled 612 will automatically import the user's age and gender information data into the internal memory storage (RAM, step 1012) from the non-volatile access memory. The system simultaneously receives the blood pressure measurement value, heart rate measurement value, measurement date, hour and other data transmitted by the user terminal device. Step 1014 determines whether the above data information is complete. If "Yes", execute the next steps of the program until step 1034 generates the real-time blood pressure reference value ($BP_{ref}$).

In step 1036, the CPU executes the command to compare the blood pressure measurement value with the blood pressure reference value to describe the blood pressure status (Compare BP to describe BP status). After steps 1038→1068, the user's blood pressure status description is completed, and the system uses text, charts, tables, among other ways to display, record, and store user blood pressure status description information.

When the user's blood pressure status is described as abnormal blood pressure, the CPU executes steps 1052 and 1064, flashes and marks the abnormal blood pressure values and inaccurate blood pressure measurement values of steps 1048, 1062, and 1050, and starts the information prompt and medical advice prompt. The CPU sends relevant information to the user terminal through the network, while the user also has the authority to log in to the system to query relevant information at any time.

The terms "first" and "second" are used for descriptive purposes only and are not to be construed as indicating or implying a relative importance or implicitly indicating the number of technical features indicated. Thus, elements referred to as "first" and "second" may include one or more of the features either explicitly or implicitly. In the description of the present disclosure, "a plurality" indicates two or more unless specifically defined otherwise.

In the description of the present disclosure, the terms "some embodiments," or "example," and the like may indicate a specific feature described in connection with the embodiment or example, a structure, a material or feature included in at least one embodiment or example. In the present disclosure, the schematic representation of the above terms is not necessarily directed to the same embodiment or example.

Moreover, the particular features, structures, materials, or characteristics described may be combined in a suitable manner in any one or more embodiments or examples. In addition, various embodiments or examples described in the specification, as well as features of various embodiments or examples, may be combined and reorganized.

In some embodiments, the control and/or interface software or applications (apps) can be provided in a form of a non-transitory computer-readable storage medium having instructions stored thereon is further provided. For example, the non-transitory computer-readable storage medium may be a Read-Only Memory (ROM), a Random-Access Memory (RAM), a Compact Disc Read-Only Memory (CD-ROM), a magnetic tape, a floppy disk, optical data storage equipment, a flash drive such as a USB drive or an SD card, and the like.

Implementations of the subject matter and the operations described in this disclosure can be implemented in digital electronic circuitry, or in computer software, firmware, or hardware, including the structures disclosed herein and their structural equivalents, or in combinations of one or more of them. Implementations of the subject matter described in this disclosure can be implemented as one or more computer programs, i.e., one or more modules of computer program instructions, encoded on one or more computer storage medium for execution by, or to control the operation of, data processing apparatus.

Alternatively, or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them.

Moreover, while a computer storage medium is not a propagated signal, a computer storage medium can be a source or destination of computer program instructions encoded in an artificially-generated propagated signal. The computer storage medium can also be, or be included in, one or more separate components or media (e.g., multiple CDs, disks, drives, or other storage devices). Accordingly, the computer storage medium may be tangible.

The operations described in this disclosure can be implemented as operations performed by a data processing apparatus on data stored on one or more computer-readable storage devices or received from other sources.

While this specification contains many specific implementation details, these should not be construed as limitations on the scope of any claims, but rather as descriptions of features specific to particular implementations. Certain features that are described in this specification in the context of separate implementations can also be implemented in combination in a single implementation. Conversely, various features that are described in the context of a single implementation can also be implemented in multiple implementations separately or in any suitable subcombination.

Moreover, although features can be described above as acting in certain combinations and even initially claimed as such, one or more features from a claimed combination can in some cases be excised from the combination, and the claimed combination can be directed to a subcombination or variation of a subcombination Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the implementations described above should not be understood as requiring such separation in all implementations, and it should be understood that the described program components and systems can generally be integrated together in a single software product or packaged into multiple software products.

As such, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking or parallel processing can be utilized.

Some other embodiments of the present disclosure can be available to those skilled in the art upon consideration of the specification and practice of the various embodiments disclosed herein. The present application is intended to cover any variations, uses, or adaptations of the present disclosure following general principles of the present disclosure and include the common general knowledge or conventional technical means in the art without departing from the present disclosure. The specification and examples can be shown as illustrative only, and the true scope and spirit of the disclosure are indicated by the following claims.

What is claimed is:

1. A mobile terminal comprising:
   a processor; and
   memory storing instructions for execution by the processor to implement:
   receiving a blood pressure measurement value (BP) and a heart rate measurement value (HR);
   obtaining blood pressure fluctuation factor parameter information based on age, gender, measurement date, and measurement time of a user;
   searching a blood pressure fluctuation value database according to the obtained blood pressure fluctuation factor parameter information, and obtaining blood pressure fluctuation values including an age-related blood pressure fluctuation value ($\Delta BP_{age}$), a measurement-time-related blood pressure fluctuation value ($\Delta BP_{hour}$), and a measurement-date-related blood pressure fluctuation value ($\Delta BP_{date}$);
   determining a real-time blood pressure reference value ($BP_{ref}$) from an ideal blood pressure ($BP_{ideal}$) and the blood pressure fluctuation values from $BP_{ref} = BP_{ideal} + \Delta BP_{age} + \Delta BP_{date} + \Delta BP_{hour}$;
   obtaining a blood pressure status according to a blood pressure ratio ($BP_{ratio}$)=BP/$BP_{ref}$; and
   displaying and storing the $BP_{ref}$, the BP, and the $BP_{ratio}$.

2. The mobile terminal according to claim 1, wherein:
   outlier blood pressure measurements are eliminated based on a heart rate fluctuation ratio $HR_{ratio}$=HR/$HR_{average} \geq 110\%$, wherein $HR_{average}$ is an average value of the HR.

3. A medical health monitoring system comprising the mobile terminal according to claim 1, further comprising a processing circuit; a storage device for storing instructions and databases; a data transmission system; and a server; wherein:
   the processing circuit is configured to execute instructions to perform operations, including receiving user data information and requesting a connection through the server; and
   the storage device includes a non-transitory storage medium.

4. The medical health monitoring system according to claim 3, wherein:
   the blood pressure status is displayed based on comparing the BP with a blood pressure threshold.

* * * * *